United States Patent
Castro et al.

(10) Patent No.: US 6,452,012 B1
(45) Date of Patent: Sep. 17, 2002

(54) 3-PHENYL-2,6-DIOXOPIPERIDIN-3-YLPROPIONAMIDE DERIVATIVES AND METHOD FOR PREPARING SAME

(75) Inventors: Bertrand Castro, Saint Aunes (FR); Hélène Mattras, Pignan (FR); Aldo Previero, Chapelle sur Glane (CH)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 10/008,892

(22) Filed: Nov. 13, 2001

Related U.S. Application Data

(62) Division of application No. 09/857,885, filed as application No. PCT/FR99/02971 on Dec. 1, 1999, now Pat. No. 6,342,607.

(30) Foreign Application Priority Data

Dec. 15, 1998 (FR) .............................................. 98 16088

(51) Int. Cl.[7] ...................... C07D 211/88; C07D 265/30
(52) U.S. Cl. ...................... 546/220; 544/168; 548/568; 548/953; 562/512; 562/553
(58) Field of Search .................................. 546/220, 226; 562/512, 553; 548/568, 953; 544/168

(56) References Cited

U.S. PATENT DOCUMENTS

| | | |
|---|---|---|
| 5,741,910 A | 4/1998 | Bichon et al. |
| 5,942,523 A | 8/1999 | Bichon et al. |
| 6,008,360 A | 12/1999 | Camus et al. |
| 6,028,082 A | 2/2000 | Bichon et al. |

FOREIGN PATENT DOCUMENTS

| | | |
|---|---|---|
| EP | 673928 | 9/1995 |
| WO | WO 97/10211 | 3/1997 |
| WO | WO 97/32852 | 9/1997 |
| WO | WO 98/05640 | 2/1998 |
| WO | WO 99/01451 | 1/1999 |

*Primary Examiner*—Charanjit S. Aulakh
(74) *Attorney, Agent, or Firm*—Michael D. Alexander; Paul E. Dupont

(57) ABSTRACT

This invention relates to 3-(3-phenyl-2,6-dioxopiperidin-3-yl) propionamide derivatives, and to processes for preparing the same.

4 Claims, No Drawings

3-PHENYL-2,6-DIOXOPIPERIDIN-3-YLPROPIONAMIDE DERIVATIVES AND METHOD FOR PREPARING SAME

CROSS REFERENCE TO RELATED APPLICATIONS

This application is a divisional of prior copending application, Ser. No. 09/857,885, filed Jun. 12, 2001, now U.S. Pat. No. 6,342,607, U.S.C. 371 application of PCT International application No. PCT/FR99/02971, filed Dec. 1, 1999, which in turn claims priority from French application No. 98/16088, filed Dec. 15, 1998.

The subject of the present invention is 3-(3-phenyl-2,6-dioxopiperidin-3-yl)propionamide derivatives, their method of preparation and their use.

3-(3,4-dichlorophenyl)-2,6-dioxopiperidine-3-propionic acid is described in patent application WO 97/32852.

There has now been found a novel compound of formula:

(I)

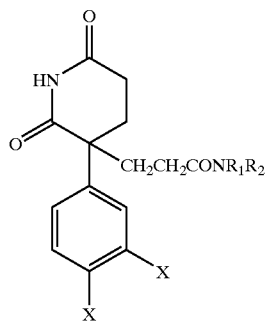

in which:

X represents a halogen, preferably a chlorine atom or fluorine atom;

$R_1$ and $R_2$ each independently represent hydrogen, a $C_1$–$C_6$ alkyl which is unsubstituted or substituted with a hydroxyl, a benzyl which is unsubstituted or substituted with a $C_1$–$C_4$ alkyl, a hydroxyl or $R_1$ and $R_2$ together constitute with the nitrogen atom to which they are attached a heterocyclic radical chosen from azetidin-1-yl, pyrrolidin-1-yl, piperidin-1-yl and morpholin-4-yl, it being possible for said heterocyclic radicals to be mono- or disubstituted.

As substituents of said heterocyclic radicals, there may be mentioned groups, which are similar or different, chosen from a $C_1$–$C_4$ alkyl, a phenyl, a benzyl, an amino, a ($C_1$–$C_4$)alkylamino and a di($C_1$–$C_4$) alkylamino.

Compound (I) exists in racemic form or in 2 enantiomerically pure forms. There is preferred the compound having the configuration described by the formula:

(II)

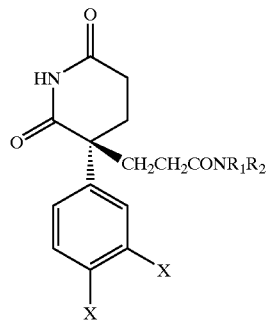

There are preferred the compounds of formula (I) or of formula (II) in which $NR_1R_2$ represents a dialkylamino group such as dimethylamino, butylamino, ethanolamino, (N-methyl) ethanolamino, benzylamino, morpholino or piperidino. There are also preferred the compounds of formula (I) or of formula (II) in which $NR_1R_2$ represents a 4-methylamino-4-phenylpiperdin-1-yl group.

The compounds of formula (I) or of formula (II) are intermediates which are useful for the preparation of the compounds of formula:

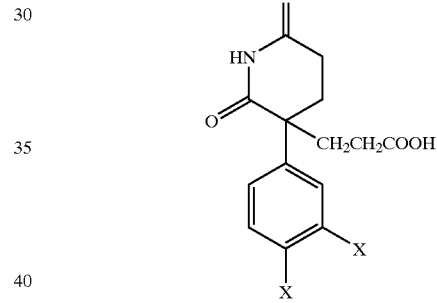

or (IV)

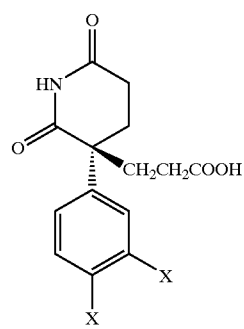

in which X is as defined above for (I).

It appears in patent application WO 97/03852 that the compounds of formula (III) or (IV) are useful for the preparation of neurokinin antagonist compounds such as that described in the publication by X. Emonds-Alt et al., Life Sci., 1995, 56 (1), 27–32, namely (S)-N-[1-[3-{1-benzoyl-3-(3,4-dichlorophenyl)piperidin-3-yl}propyl]-4-phenylpiperidin-4-yl]-N-methylacetamide or SR 142801 whose international nonproprietary name is osanetant. This compound is an $NK_3$ antagonist.

In particular, the subject of the present invention is a compound of formula:

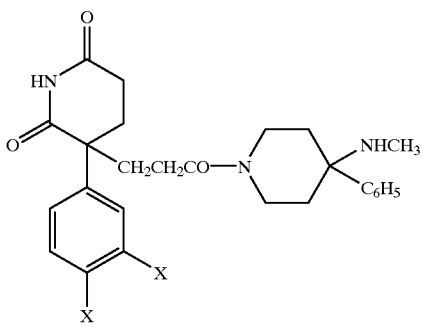

(V)

in which X is as defined above for (I).

The subject of the present invention is also a method of preparing a compound of formula (I). Said method is characterized in that a compound of formula:

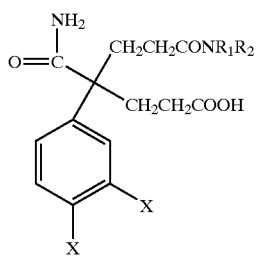

(VI)

in which X is as defined above for (I), is cyclized by elimination of water.

The compound of formula (VI) may be obtained by the action of an amine of formula $HNR_1R_2$ in which $R_1$ and $R_2$ are as defined above for (I) on a compound of formula:

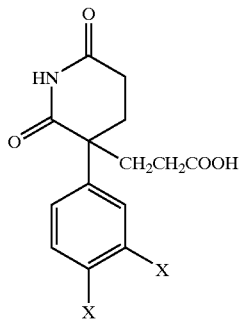

(III)

The preparation of the compound of formula (VI) is carried out in water, in an alcoholic solvent, in an ethereal solvent, in a chlorinated solvent or in an aromatic solvent, at a temperature between room temperature and the reflux temperature of the solvent. Preferably, water or methanol is used.

The cyclization of the compound of formula (VI) by elimination of a molecule of water is carried out after activation of the carboxyl group of the compound of formula (VI) by formation of a mixed anhydride. For that, an anhydride is used in excess, for example acetic anhydride or methanesulfonic anhydride, at a temperature between room temperature and 100° C.

The compounds of formula (VI) are novel and form part of the present invention.

The compounds of formula (III) are described in patent application WO 97/32852.

According to the present invention, it has been observed that starting with a compound of formula (III) in racemic form, a racemic compound of formula (VI) is obtained in which the 2 enantiomers are in the same proportion as for the starting compound. A racemic compound of formula (I) is then obtained by cyclization in which the 2 enantiomers are in the same proportion as for the starting compound.

According to the present invention, it has been found, using as starting material a pure enantiomer of the compound of formula (III), that the formation of the hexanoic acid derivative of formula (VI) occurs with retention of configuration, and that the cyclization then occurs with inversion of configuration.

The method according to the invention thus applies to the preparation of compounds in optically pure form. Thus, advantageously, the present invention relates to a method for the preparation of a compound of formula (II) characterized in that a compound of formula:

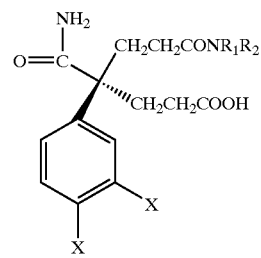

(VII)

in which X is as defined above for (I), is cyclized by elimination of water, to give a compound of formula:

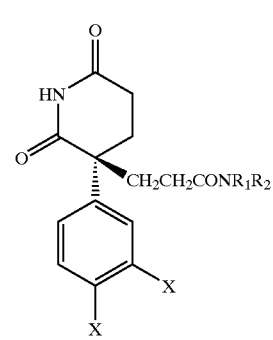

(II)

The compound of formula (VII) may be obtained by the action of an amine of formula $HNR_1R_2$ in which $R_1$ and $R_2$ are as defined above for (I) on a compound of formula:

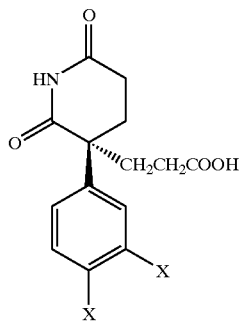

(IVa)

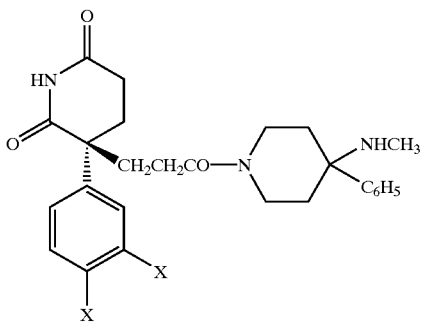

(IX)

According to the present invention, the compound of formula (I) may be prepared using another method characterized in that an amine of formula $HNR_1R_2$ in which $R_1$ and $R_2$ are as defined above for (I) is reacted with a compound of formula:

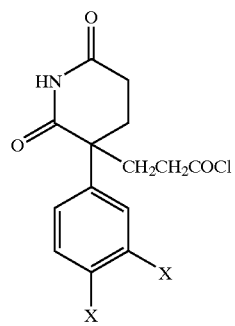

(VIII)

in which X is as defined above for (I).

The compounds of formula (VIII) may be obtained from an acid of formula:

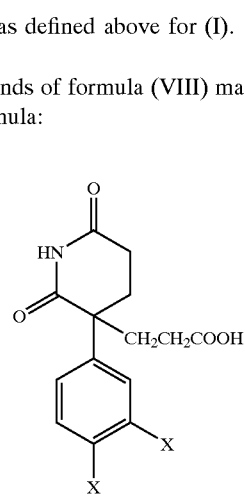

(III)

The compounds of formula (VIII) are novel and constitute a subsequent aspect of the present invention.

The action of an amine on an acid chloride of formula (VIII) is preferred for the preparation of a compound of formula (V) and most particularly-for the preparation of an enantiomer of the compound of formula (V) of formula:

This method is characterized in that 4-methylamino-4-phenylpiperidine is reacted with a compound of formula:

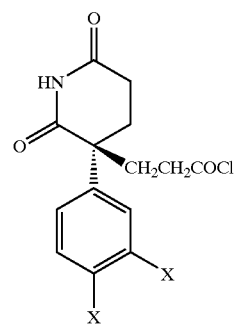

(X)

The compound of formula (X) may be prepared from the acid of formula:

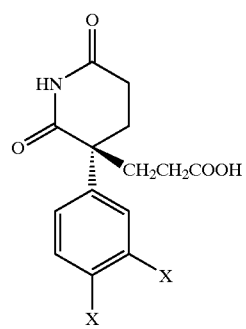

(IV)

The acid chloride is prepared in a known manner, for example by the action of thionyl chloride in the absence of solvent or in an anhydrous solvent such as toluene, dimethylformamide or dichloromethane or alternatively in a mixture of these solvents.

The action of 4-methylamino-4-phenylpiperidine is carried out in an anhydrous solvent, in a basic medium, for example in the presence of triethylamine.

The 4-methylamino-4-phenylpiperidine is prepared according to Biorg. Med. Chem. Letters, 1996, 4 (19), 2307–2310.

According to the present invention, the compound of formula (I) makes it possible to obtain, by acidolysis, the acid of formula (III). Likewise, according to the present invention, the compound of formula (II) makes it possible to obtain, by acidolysis, the acid of formula:

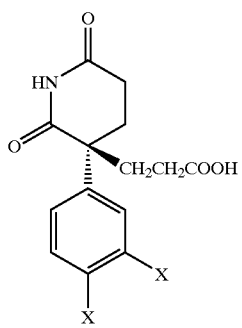

(IV)

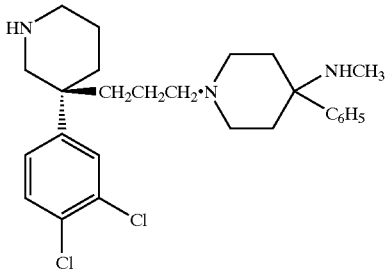

(XII)

The acidolysis is carried out in a manner known to persons skilled in the art, for example with a $C_1$–$C_4$ carboxylic acid.

Thus, the present invention relates to a method of preparing a compound of formula (III) by hydrolysis of a compound of formula (I). It also relates to a method of preparing a compound of formula (IV) by hydrolysis of a compound of formula (II).

According to a subsequent aspect of the resent invention, the compound of formula (I) makes it possible to obtain, by reduction, a compound of formula:

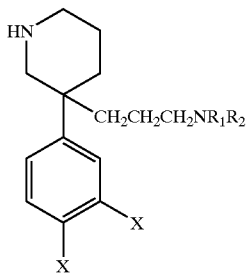

(XI)

in which X, $R_1$ and $R_2$ are as defined for (I).

The reduction is carried out by means known to persons skilled in the art. The reducing agents used are borane complexes such as for example borane-tetrahydrofuran or borane-dimethyl sulfide or alternatively a mixed alkali metal hydride such as lithium aluminum hydride or sodium bis(2-methoxyethoxy)aluminum hydride in solution in toluene (Red-Al®, the borane-tetrahydrofuran complex being preferred.

The reduction with borane is carried out in a solvent, preferably an aprotic solvent such as tetrahydrofuran at the reflux temperature of the solvent. In general, after 1 to 6 hours of heating, the reduction is complete and the 3,3-disubstituted piperidine is isolated, according to conventional methods, by first destroying the excess borane with methanol. The free base may be isolated by evaporation of the solvent, and then the residue is taken up in water, the medium is acidified with hydrochloric acid, treated with a base, preferably sodium hydroxide, and extracted with a solvent.

Most particularly, by reducing a compound of formula (IX) in which X=Cl, there is prepared a compound of formula:

Thus, the present invention relates to a method of preparing a compound of formula (XI) by reducing a compound of formula (I).

Likewise, the present invention relates to a method of preparing a compound of formula (XII) by reducing a compound of formula (IX).

In the examples and in the description, the following abbreviations are used.

RT: room temperature
Me: methyl
THF: tetrahydrofuran
DMF: dimethylformamide
L-PheOMe: methyl ester of L-phenylalanine
BOP (Castro's reagent): benzotriazol-1-yloxytris (dimethylamino)phosphonium hexafluorophosphate
MIBK: methyl isobutyl ketone.

The NMR (nuclear magentic resonance) spectra are recorded at 250 or 300 MHz.

To analyze the products, high-performance liquid chromatography on $C_{18}$ (HPLC-C18) is used under the following conditions:

10 to 15 µmol of product dissolved in 50 µl of methanol are diluted with 150 µl of eluent, and 20 µl are injected onto an Alltima® C18 5 µcolumn (length=250 mm, inside diameter=4.6 mm) eluting with an isocratic mixture A/B:32/68, the flow rate 1 ml/min; A: aqueous buffer 2.6; B: methanol; the compounds are detected at 280 nm.

Chiral HPLC-C18 is also used under the following analytical conditions:

2 to 3 µmol of product are dissolved in a mixture of DMF (100 µl), triethylamine (15 µl), with either (S)-methylbenzylamine (15 µl), or L-PheOMe (15 mg). 10 mg of BOP (Castro's reagent) are added and the medium is left for 30 minutes at 50° C. The reaction mixture is subjected to an acid extraction with ethyl acetate/HCl 1N:1 ml/1 ml. 100 µl of organic phase are then evaporated off, then the medium is either taken up in 250 >l of eluent or taken up in 50 µl of methanol and then diluted with 150 µl of eluent. 20 µl of this solution are injected. The procedure is carried out on columns 250 mm long, having an inside diameter of 4.6 mm, eluting with a hexane/isopropanol:70/30 mixture, flow rate 1 ml/min. The compounds are detected at 280 nm.

The other analytical conditions vary according to the compounds analyzed.

PREPARATION 1

4,6-Dicarbamoyl-4-(3,4-dichlorophenyl)hexanoic Acid.

X=Cl, NR₁R₂=NH₂            (VI)

3.30 g of racemic 3-(3,4-dichlorophenyl)-2,6-dioxopiperidine-3-propionic acid are placed in 20 ml of an aqueous solution of aqueous ammonia at 30% and stirred at room temperature. After 2 hours, the solution is degassed under vacuum to remove the excess aqueous ammonia and then diluted to 50 ml with water. The medium is slowly acidified to pH 2–3 With 1 N HCl. The precipitate formed is filtered, drained and then dried over KOH to give 3.13 g of the expected compound.

¹H NMR (DMSO): 1.79 to 2.12 ppm (4 CH₂, m); 7.43 ppm (1 aromatic H, s); 7.60 and 7.24 ppm (2 aromatic H, d); 6.7 and 7.22 ppm (NH₂ groups).

The starting compound and the compound obtained are subjected to analysis by HPLC-C18; the retention times are Tr=6.2 minutes and Tr=3.7 minutes respectively.

Furthermore, the product obtained is subjected to chiral analysis by HPLC-C18 after coupling of its free carboxyl with L-PheOMe. 2 peaks are observed (Tr=9.8 minutes and Tr=10.7 minutes) showing that the product obtained is in racemic form.

PREPARATION 2

4,6-Dicarbamoyl-4-(3,4-dichlorophenyl)hexanoic Acid, of S Configuration

X=Cl, NR₁R₂=NH₂            (VIII)

The procedure is carried out as described in preparation 1, starting with 3.30 g of 3-[3-(3,4-dichlorophenyl)-2,6-dioxopiperidin-3-yl]propionic acid, of (S) configuration. 3.13 g of the expected compound are obtained whose analysis is carried out by HPLC-C18. A peak is observed at Tr=3.74 minutes. Chiral analysis after coupling with L-PheOMe gives a principal peak at 10.7 minutes and a secondary peak at Tr=9.8 minutes. It is observed that the optical purity is the same as that for the starting compound.

PREPARATION 2a

4,6-Dicarbamoyl-4-(3,4-dichlorophenyl)hexanoic Acid, of R Configuration

X=Cl, NR₁R₂=NH₂.            [lacuna]

The procedure is carried out as in preparation 2 using as starting material 3-[3-(3,4-dichlorophenyl)-2,6-dioxopiperidin-3-yl]propionic acid, R isome.

Chiral analysis after coupling with L-PheOMe gives a principal peak at Tr=9.8 minutes and a secondary peak at Tr=10.7 minutes.

PREPARATION 3

4-Carbamoyl-4-(3,4-dichlorophenyl)-6-(piperidin-1-yl)carbonylhexanoic Acid

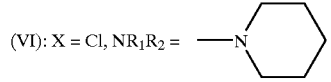

(VI): X = Cl, NR₁R₂ =

0.3 g of racemic 3-[3-(3,4-dichlorophenyl)-2,6-dioxopiperidin-3-yl]propionic acid, 1 ml of methanol and 0.5 ml of piperidine are placed at 60° C. for 15 hours in a round-bottomed flask. The reaction medium is diluted with 10 ml of water and acidified with 1 N HCl to pH 2–3. The white crystals formed are filtered, drained and then dried to give 0.3 g of the expected compound.

¹H NMR (DMSO): 1.36 to 1.56 ppm (3 CH₂, m) ; 2.04 to 2.50 ppm (4 CH₂, m); 3.3 ppm (2 CH₂, m); 7.25 and 7.6 ppm (2 aromatic H, d); 7.45 ppm (1 aromatic H, d); 10.98 ppm (COOH, s).

HPLC-C18 analysis shows a peak at Tr=8.2 minutes. The HPLC-C18 chiral analysis, after coupling with L-PheOMe, shows the formation of 2 peaks of identical surface area: Tr=7.9 minutes and Tr=8.8 minutes.

The compound obtained is therefore in racemic form.

PREPARATION 4

4-Carbamoyl-4-(3,4-dichlorophenyl)-6-(piperidin-1-yl)carbonylhexanoic Acid, of S Configuration

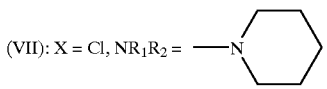

(VII): X = Cl, NR₁R₂ =

0.3 g of 3-[3-(3,4-dichlorophenyl)-2,6-dioxopiperidin-3-yl]propionic acid of S configuration is treated with piperidine as described in Preparation 3 to give 0.3 g of the expected compound.

HPLC-C18 analysis shows a peak at Tr=8.2 minutes. HPLC-C18 chiral analysis after coupling with L-PheOMe shows a peak at Tr=8.8 minutes. It is observed that the optical purity is identical to that of the starting material.

$\alpha_D^{20}$=−6.4°(c=1; CH₃OH/NaOH1 N:9.7/0.3).

PREPARATION 4a

4-Carbamoyl-4-(3,4-dichlorophenyl)-6-(piperidin-1-yl)carbonylhexanoic Acid, of R Configuration

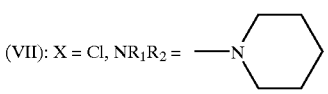

(VII): X = Cl, NR₁R₂ =

The procedure is carried out as in preparation 4 using as starting material 3-(3-(3,4-dichlorophenyl)-2,6-dioxopiperidin-3-yl]propionic Acid of R Configuration.

Chiral analysis after coupling with L-PheOMe shows a peak at Tr=7.9 minutes.

By carrying out the procedure as in Preparations 1 and 3 described above, starting with racemic 3-[3-(3,4-dichlorophenyl)-2,6-dioxopiperidin-3-yl]propionic acid and various amines, the compounds described in Table 1 below were prepared.

These compounds are characterized in HPLC by their capacity factor.

By way of comparison, the $k^1$ values are indicated for the compounds of Preparations 1 and 3.

TABLE 1

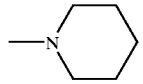

(VI)

| Preparations | —NR₁R₂ | k' |
|---|---|---|
| 1 | —NH₂ | 0.86 |
| 3 | piperidinyl | 2.73 |
| 5 | —NHCH₂CH₂OH | 0.72 |
| 6 | —N(CH₃)—CH₂CH₂OH | 0.86 |
| 7 | morpholinyl | 1.17 |
| 8 | —HN(CH₂)₃CH₃ | 3.0 |
| 9 | —NH—CH₂—C₆H₅ | 3.25 |

EXAMPLE 1

3-(3,4-Dichlorophenyl)-3-[(piperidin-1-yl)-3oxopropyl]piperidine-2,6-dione

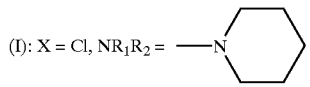

(I): X = Cl, NR₁R₂ = —N(piperidine)

0.3 g of the compound obtained in Preparation 3 is placed in a closed container with 1.5 ml of acetic anhydride and heated at 95–100° C. for 30 minutes. After cooling to RT, ethyl ether is added and the medium is allowed to stand in a cold room at 4° C. The crystals formed are filtered and drained to give 270 mg of the expected compound.

HPLC-C18 analysis shows a single peak at Tr=14 minutes. This product which is obtained is identical to that which is obtained by coupling 3-[3-(3,4-dichlorophenyl)-2,6-dioxopiperidin-3-yl]propionic acid with piperidine.

EXAMPLE 2

3-(3,4-Dichlorophenyl)-3-[(piperidin-1-yl)-3-oxopropyl]piperidine-2,6-dione, of R Configuration

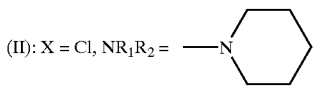

(II): X = Cl, NR₁R₂ = —N(piperidine)

0.2 g of the compound obtained in Preparation 4 and 0.8 ml of acetic anhydride are placed in a closed tube at 95–100° C. for 30 minutes. After cooling to RT, 10 ml of distilled water are added and the medium is left stirring for 30 to 40 minutes. The medium is extracted with 10 ml of ethyl acetate and then the ethyl acetate phase is dried and then evaporated under reduced pressure. 0.18 g of the expected compound is obtained. HPLC-C18 analysis shows a single peak at Tr=14 minutes.

EXAMPLE 2a 3-(3,4-Dichlorophenyl)-3-[(piperidin-1-yl)-3-oxopropyl]piperidine-2,6-dione, of R Configuration The procedure is carried out as in Example 2, starting with the compound obtained in preparation-4a.

HPLC-C18 analysis of the compound obtained shows a single peak at Tr=14 minutes.

EXAMPLE 3

3-[3-(3,4-Dichlorophenyl)-2,6-dioxopiperidin-3-yl] propionic Acid, of S Configuration X=Cl. (III)

The compound obtained in EXAMPLE 2 is taken up in 0.5 ml of propionic acid and placed in a tube sealed under vacuum. After 18 hours at 145° C., the reaction mixture and diluted with 10 ml of 1 N HCl. After one day, the product which crystallizes is filtered, drained and dried. 100 mg of the expected compound are obtained.

HPLC-C18 analysis shows a peak at Tr=6.2 minutes.
Chiral analysis after coupling with (S)-methylbenzylamine shows a peak at 7.13 minutes.

EXAMPLE 3a

3-[3-(3,4-Dichlorophenyl)-2,6-dioxopiperidin-3-yl] propionic Acid, of S Configuration The procedure is carried out as in Example 3 starting with the compound obtained in Example 2a.

HPLC-C18 analysis of the compound obtained shows a peak at Tr=6.2 minutes.

Chiral analysis after coupling with (S)-methylbenzylamine shows a peak at 9.13 minutes.

EXAMPLE 4

3-(3,4-Dichlorophenyl)-3-[3-(4-methylamino-4-phenylpiperidin-1-yl)-3-oxopropyl]piperidine-2,6-dione, of S Configuration X=Cl (IX)

3-[3-(3,4-Dichlorophenyl)-2,6-dioxopiperidin-3-yl] propionic Acid Chloride, of S Configuration.

Under a nitrogen atmosphere, 20 g of 3-[3-(3,4-dichlorophenyl)-2,6-dioxopiperidin-3-yl]propionic acid, 200 ml of toluere and 0.5 ml of DMF are mixed. The medium is heated to 60° C. and 14.9 g of thionyl chloride and 40 ml of toluene are introduced dropwise. The stirring is maintained for 5 hours at 60° C. The toluene and the excess thionyl chloride are evaporated off and then the reaction medium is dried in an oven (40° C.) overnight.

The product obtained is used as it is in the next stage.

B) 3-(3,4-Dichlorophenyl)-3-[3-(4-methylamino-4-phenylpiperidin-1-yl)-3-oxopropyl]piperidine-2,6-dione, of S Configuration.

Under a nitrogen atmosphere, 11.5 g of 4-methylamino-4-phenylpiperidine in solution in 100 ml of THF and 8.52 ml of triethylamine are introduced and then the reaction medium is cooled to 0° C.±5° C. with an ice bath. The acid chloride prepared in the preceding stage in 150 ml of THF is added dropwise and the medium is left stirring for one hour. After evaporation of the THF, the medium is washed with 100 ml of water and 100 ml of dichloromethane. The organic phase is separated after settling out and then washed 3 times with 100 ml of water; the dichloromethane is evaporated off and then the medium is dried in an oven at 40° C. and 32.1 g of the expected compound are obtained. 29.1 g of this compound are recrystallized in the hot state from MIBK to give 17 g of the pure compound. Moreover, the recrystallization mother liquors are filtered on silica to give an additional 5.2 g of pure compound.

$^1$H NMR (CDCl$_3$): 1.65 to 2.69 ppm (16 H, m); 3.25 to 3.98 ppm (4 H, m); 7.06 to 7.46 ppm (8 aromatic H and CO—NH—CO); $\alpha_d^{25}$=+77.8° (c=1, methanol).

What is claimed is:

1. A compound of formula:

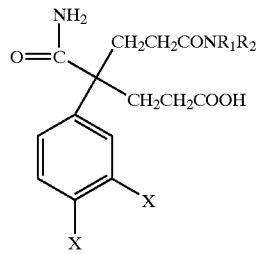

(VI)

wherein

X represents a halogen;

R$_1$ and R$_2$ each independently represent hydrogen, a C$_1$–C$_6$ alkyl which is unsubstituted or substituted with a hydroxyl, a benzyl which is unsubstituted or substituted with a C$_1$–C$_4$ alkyl, a hydroxyl or R$_1$ and R$_2$ together constitute with the nitrogen atom to which they are attached a heterocyclic radical chosen from azetidin-1-yl, pyrrolidin-1-yl, piperidin-1-yl and morpholin-4-yl, it being possible for said heterocyclic radicals to be mono- or disubstituted.

2. A compound according to claim 1 of formula:

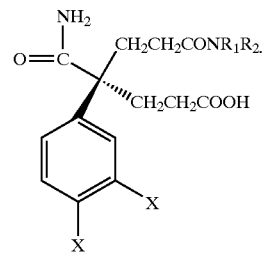

(VII)

3. A compound of formula:

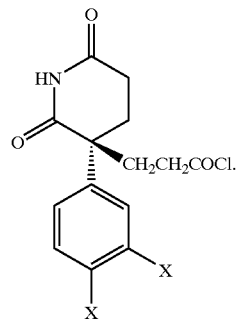

(VIII)

wherein X represents a halogen.

4. A compound according to claim 3 of formula:

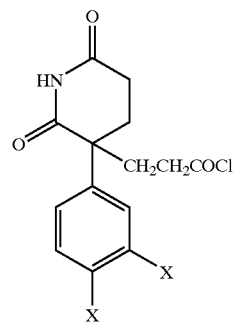

(X)

* * * * *